(12) United States Patent
Kennedy

(10) Patent No.: US 7,187,967 B2
(45) Date of Patent: Mar. 6, 2007

(54) APPARATUS AND METHOD FOR DETECTING NEURAL SIGNALS AND USING NEURAL SIGNALS TO DRIVE EXTERNAL FUNCTIONS

(75) Inventor: Philip R. Kennedy, Duluth, GA (US)

(73) Assignee: Neural Signals, Inc., Atlanta, GA (US)

( * ) Notice: Subject to any disclaimer, the term of this patent is extended or adjusted under 35 U.S.C. 154(b) by 50 days.

(21) Appl. No.: 10/675,703

(22) Filed: Sep. 30, 2003

(65) Prior Publication Data
US 2005/0070810 A1 Mar. 31, 2005

(51) Int. Cl.
*A61B 5/04* (2006.01)
(52) U.S. Cl. ..................... 600/544; 600/378
(58) Field of Classification Search ........ 600/372–375, 600/544
See application file for complete search history.

(56) References Cited

U.S. PATENT DOCUMENTS

| | | | |
|---|---|---|---|
| 4,533,346 A * | 8/1985 | Cosgrove et al. ............. | 604/66 |
| 4,852,573 A | 8/1989 | Kennedy | |
| 6,597,954 B1 * | 7/2003 | Pless et al. ................... | 607/62 |
| 6,647,296 B2 * | 11/2003 | Fischell et al. ............... | 607/45 |
| 6,920,351 B2 * | 7/2005 | Mitra et al. .................. | 600/544 |
| 2004/0082875 A1 * | 4/2004 | Donoghue et al. .......... | 600/544 |

OTHER PUBLICATIONS

Kennedy, et al., Behavioral Correlates of Action Potentials Recorded Chronically Inside the Cone Electrode; NeuroReport 3,605-608 (1992); 4 Pages.
Kennedy and Bakay, Restoration of Neural Output from a Paralyzed Patient by a Direct Brain Connection; Rapid Science Ltd., vol. 9, No. 8, Jun. 1998; 5 Pages.
Kennedy, The Cone Electrode: A Long-term Electrode that Records from Neurites Grown Onto its Recording Surface; Bioengineerin Center, Georgia Institute of Technology, Atlanta, GA; 1989 Elsevier Science Publishers B.V. (Biomedical Division).

* cited by examiner

*Primary Examiner*—Robert L. Nasser
(74) *Attorney, Agent, or Firm*—Bryan W. Bockhop; Bockhop & Associates, LLP

(57) ABSTRACT

A system and method for capturing a neural signal inside a patient's skull, transmitting it to a remote receiver, and using it to control an application. A plurality of skull screws is inserted on the skull and under the scalp, and the skull screws are connected to a transmitter. The differential potential between two skull screws are detected, amplified, and transmitted to a receiver connected to a computing device. The computing device checks for the signal's voltage level and duration before using it for controlling the application.

8 Claims, 3 Drawing Sheets

APPARATUS AND METHOD FOR DETECTING NEURAL SIGNALS AND USING NEURAL SIGNALS TO DRIVE EXTERNAL FUNCTIONS

BACKGROUND

1. Field of the Invention

The present invention generally relates to an apparatus for detecting neural activity and, more specifically, for detecting neural activity for the purpose of control of an external device.

2. Description of the Related Art

Muscle paralysis affects over one hundred thousand people in the United States and approximately one million people worldwide. One approach used to provide assistance to paralyzed people has been described by the U.S. Pat. No. 4,852,573, which is hereby incorporated by reference.

One class of patients who face severe difficulties in their daily lives is those with locked-in syndrome. Locked-in syndrome patients generally have a cognitively intact brain and a completely paralyzed body. They are alert but cannot move or talk. They face a life-long challenge to communicate. Some patients may use eye movements, blinks or remnants of muscle movements to indicate binary signals, such as "yes" or "no." To enhance communication with these patients, several devices have been developed including electroencephalographic (EEG) control of a computer. These systems can provide patients with the ability to spell words.

One approach is to implant the neocortex using a neurotrophic electrode that uses trophic factors to encourage growth of neural tissue into a hollow electrode tip that contains two wires. The neural tissue is held firmly within the tip because it grows through both ends and joins with neighboring neuropil. This has provided stable long-term recordings in rats and monkeys for up to sixteen months. The histological analysis in rats and monkeys shows normal neuropil without neurons but with an abundance of myelinated axons. Similar implantation on human patients have shown that stable brain signals can be recorded and the patients can control these signals and to use them to drive a cursor on a computer screen.

The above approach requires an intrusive insertion of neurotrophic electrodes inside of the cortex, which requires risky and delicate surgery. Thus, there is a need for a system and method that enable capturing of neural signals without an extensive and intrusive insertion of neurotrophic electrodes.

SUMMARY OF THE INVENTION

The present invention, in one aspect, is an apparatus for detecting neural signals emanating from inside a brain within a cranium that is covered by a scalp and for transmitting the signals to an external receiver. A first conductive skull screw, capable of being implanted in the cranium and under the scalp, has a predefined length that is at least as long as the thickness of the cranium, but less than a thickness that would cause the first conductive screw to invade the brain. A second conductive skull screw, capable of being implanted in the cranium and under the scalp, has a predefined length that is at least as long as the thickness of the cranium, but less than a thickness that would cause the second conductive screw to invade the brain. A transponder is electrically coupled to the first conductive skull screw and to the second conductive skull screw. The transponder is capable of being implanted between the cranium and the scalp. The transponder is also capable of detecting a differential electrical potential between the first conductive skull screw and the second conductive skull screw and generating a signal representative thereof. The transponder is also capable of transmitting the signal to the external receiver.

In another aspect, the invention is an apparatus for detecting neural signals emanating from inside a brain within a cranium that is covered by a scalp and for transmitting the signals to a processing device. A first surface electrode is placed on the scalp above the first conductive skull screw. A second surface electrode is placed on the scalp above the second conductive skull screw. An amplifier is electrically coupled to the first surface electrode and to the second surface electrode. The amplifier is capable of detecting a differential potential between the first surface electrode and the second surface electrode, thereby generating a signal representative thereof. The amplifier is also capable of transmitting the signal to the processing device.

In another aspect, the invention is a method for communicating a neural signal inside a brain to a remote receiver. A first conductive skull screw is inserted in a cranium under a scalp in a first location. A second conductive skull screw is inserted in a cranium under the scalp in a second location. The first location and the second location are chosen so that a change in neural electrical potential between the first conductive skull screw and the second conductive skull screw occurs when a patient performs a neural task. A transponder is implanted under the scalp. The transponder is electrically coupled to the first conductive skull screw and to the second conductive skull screw. The change in neural electrical potential between the first conductive skull screw and the second conductive skull screw is detected. A signal representative of the change in neural electrical potential is transmitted from the transponder to the remote receiver.

In yet another aspect, the invention is a method for communicating a neural signal inside a brain of a patient to a remote receiver. A first conductive skull screw is inserted in a cranium under a scalp in a first location adjacent to a first location. A second conductive skull screw is inserted in a cranium under the scalp in a second location. The first location and the second location are chosen so that a change in neural electrical potential between the first conductive skull screw and the second conductive skull screw occurs when a patient performs a neural task. A first surface electrode is placed on the scalp and above the first conductive skull screw. A second surface electrode is placed on the scalp and above the second conductive skull screw. The first surface electrode and the second surface electrode are electrically coupled to an amplifier. A differential electrical potential is detected between the first surface electrode and the second surface electrode. The differential electrical potential represents the neural signal. A signal corresponding to the differential electrical potential is transferred to a signal processor.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION

Figure 1:
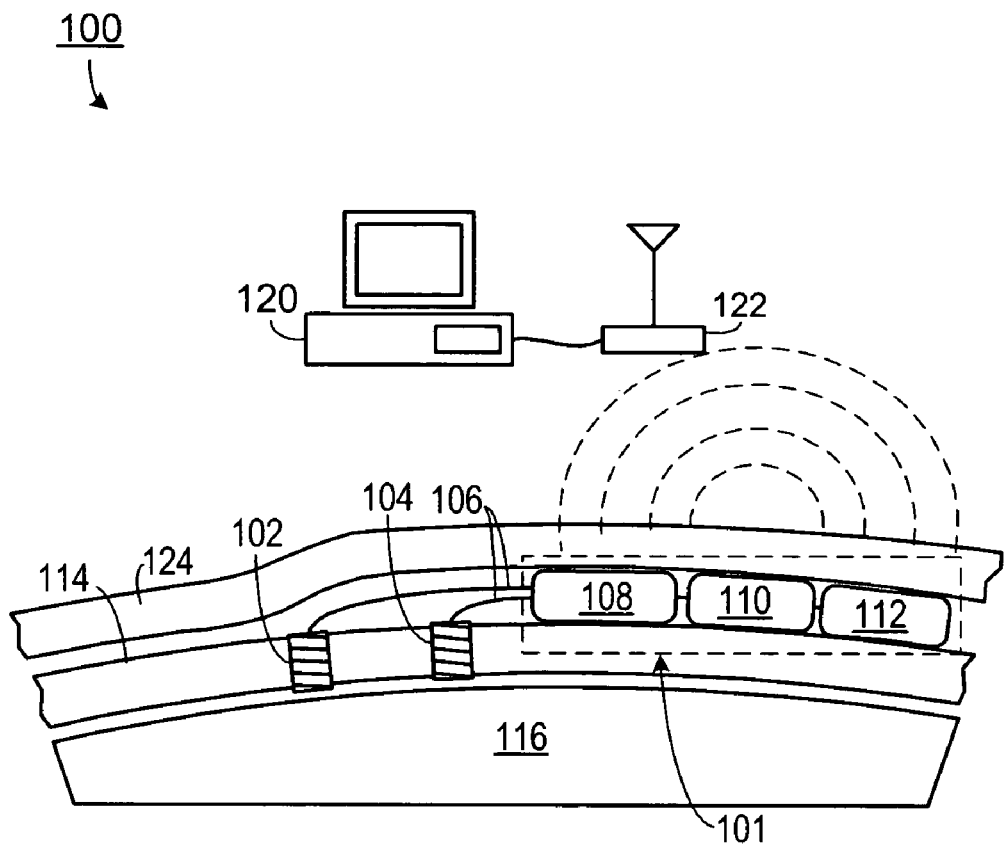
FIG. 1 is a cutaway view of an electrode implantation according to the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

The invention provides a less invasive and easier to implement brain-computer interface device and method. The method includes implantation of conductive skull screws in the skull of a patient and adjacent to the outer layers of the patient's cortex. The device receives signals from the cortex and transmits them to a nearby receiver where they are processed to drive a cursor on a computer or other electronic devices. For people suffering from "locked-in" syndrome, cortical control of the external environment can restore a means of communication via computer cursor control. Cortical control signals allow control of various assistive technology devices such as wheelchairs, or may even restore control of a paralyzed limb. These cortical signals can consist of either fast transients (FTs, such as action potentials) or local field potentials (LFPs). With training, some patients have been able to use LFPs or FTs to control virtual tools such as a keyboard cursor and a computer-simulated digit (cyber digit).

As shown in FIG. 1, one embodiment of the invention 100 includes a first conductive skull screw 102 and a second conductive skull screw 104 that are implanted in the cranium 114 of a patient. The skull screws 102 and 104, are typically made of stainless steel and each have a length corresponding at least to the thickness of the cranium 114, but are not long enough to invade the patient's brain 116 when implanted. The first skull screw 102 is placed at a first location and the second skull screw 104 is placed at a second location. The first location and the second location are chosen so that a change in neural electrical potential between the first conductive skull screw and the second conductive skull screw occurs when a patient performs a neural task. For example, if the patient generates a thought that would cause movement in an average individual, a localized neural electrical potential will be generated. This electrical potential is sensed in the patient and the first skull screw 102 may be implanted at the site of the localized neural electrical potential. The second skull screw 104 is then placed at a location near a region of the patient's cortex where the localized neural electrical potential is not sensed and, thus, serves as a reference electrode. The location may be determined through performance a functional magnetic resonance imaging (fMRI) process of the cortex.

The conductive skull screws 102 and 104 should be electrically conductive and corrosion resistant. They can be metallic screws made from stainless steel or other suitable conductive materials, such a conductive ceramic or non-metallic material. The dimensions for the conductive skull screws 102 and 104, which act like electrodes, are typically between 1/16 inches to 1/2 inches in diameter and 1/4 inches to 1 and 1/2 inches in length. Generally, the conductive skull screws 102 and 104, after implantation, are fixed in the skull without going into the brain.

A sufficient electrical potential that is measured between the first skull screw 102 and the second skull screw 104 forms a neural signal that indicates a desire on behalf of the patient determined action to take place.

The first conductive skull screw 102 and a second conductive skull screw 104 are connected via wires 106 to a transponder 101, which includes amplifier 108, a transmitter 110 and a power induction circuit 112. The amplifier 108 amplifies the neural signal sensed between the skull screws 102 and 104. The wires 106 are made from a conductive material and are insulated to prevent electrical contact with the body other than in selected areas. After amplification, the neural signal is transmitted via the wireless transmitter 110 to a remote receiver 122 that is connected to a computer 120.

The power induction circuit 112 powers the amplifier 108 and the transmitter 110. The power induction circuit 112 is responsive to an electromagnetic signal and generates electricity therefrom, thereby being capable of supplying power to the amplifier 108 and the transmitter 110 without requiring a battery. The amplifier 108, the transmitter 110, and the power induction circuit 112 may also be built into a single unit that is suitable for implantation. The conductive skull screws 102 and 104, the wires 106, the amplifier 108, the transmitter 110, and the induction circuit 112 may be minimized in size, sterilized, and implanted under the scalp 124, thereby avoiding entry of pathogenic organisms.

In one illustrative embodiment, the amplifier 108 provides a gain of about 1,000 to the voltage differential sensed between the conductive skull screws 102 and 104. The amplified signal that represents the voltage differential is then passed to the transmitter 110. The amplifier 108 may also be capable of noise reduction.

In one embodiment, the transmitter 110 is a frequency modulated (FM) transmitter. However, as is readily apparent to those of skill in the art, there are many other types of suitable transmitters, including AM.

In one embodiment, the transmitter 110 can also be a very high frequency ("VHF") FM unit employing a modulated subcarrier. This approach permits adequate range and frequency response as well as freedom from artifacts. Power consumption can be minimized (and thus useful life extended) by using low power transistors and low-drain circuitry. In addition, using a switching arrangement such as a magnetic reed switch, which applies power only when needed, can further reduce power consumption.

Since the transmitter 110, the amplifier 108, and the power induction circuit 112 are implanted in living tissue, special encapsulation procedures are required both to ensure biocompatibility and to prevent the infusion of body fluids into the circuitry, which could cause a malfunction. A suitable encapsulating material is used, such as one of the many types of polymer that have been approved for implantation. The transmitter 110 is then coated with tissue-compatible silastic or other suitable material and then sterilized. The permeable silastic will allow sterilization of the entire unit, while protecting the sealant against mechanical abrasion, which could expose an unsterilized subsurface.

Typically, the differential potential between the conductive skull screws 102 and 104 has a duration between 10 milliseconds to a few hundred milliseconds during a neural activity event.

Figure 2:
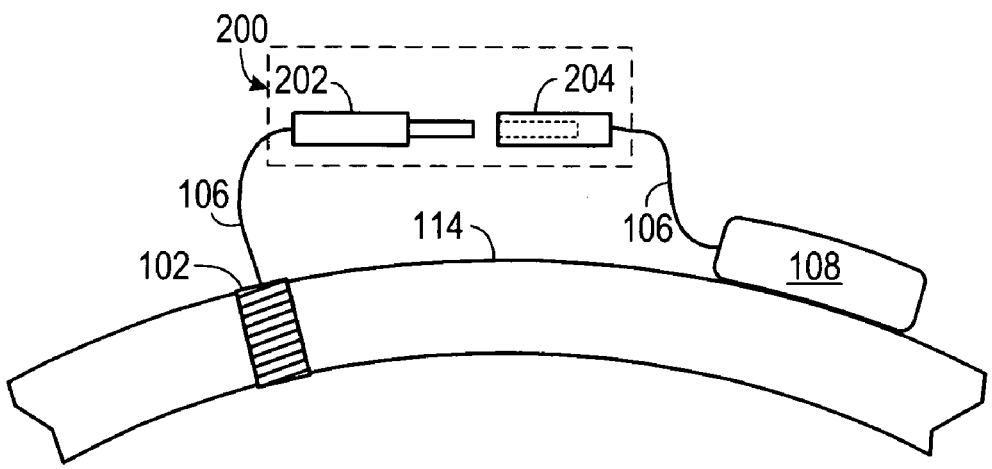
FIG. 2 illustrates an alternative embodiment of a connector connecting an electrode and the amplifier.

To facilitate connection, as shown in FIG. 2, each wire 106 may be divided into two separated sections and joined by a connector 200. The connector 200 includes a male plug 202 and a complimentary female plug 204.

Figure 3:
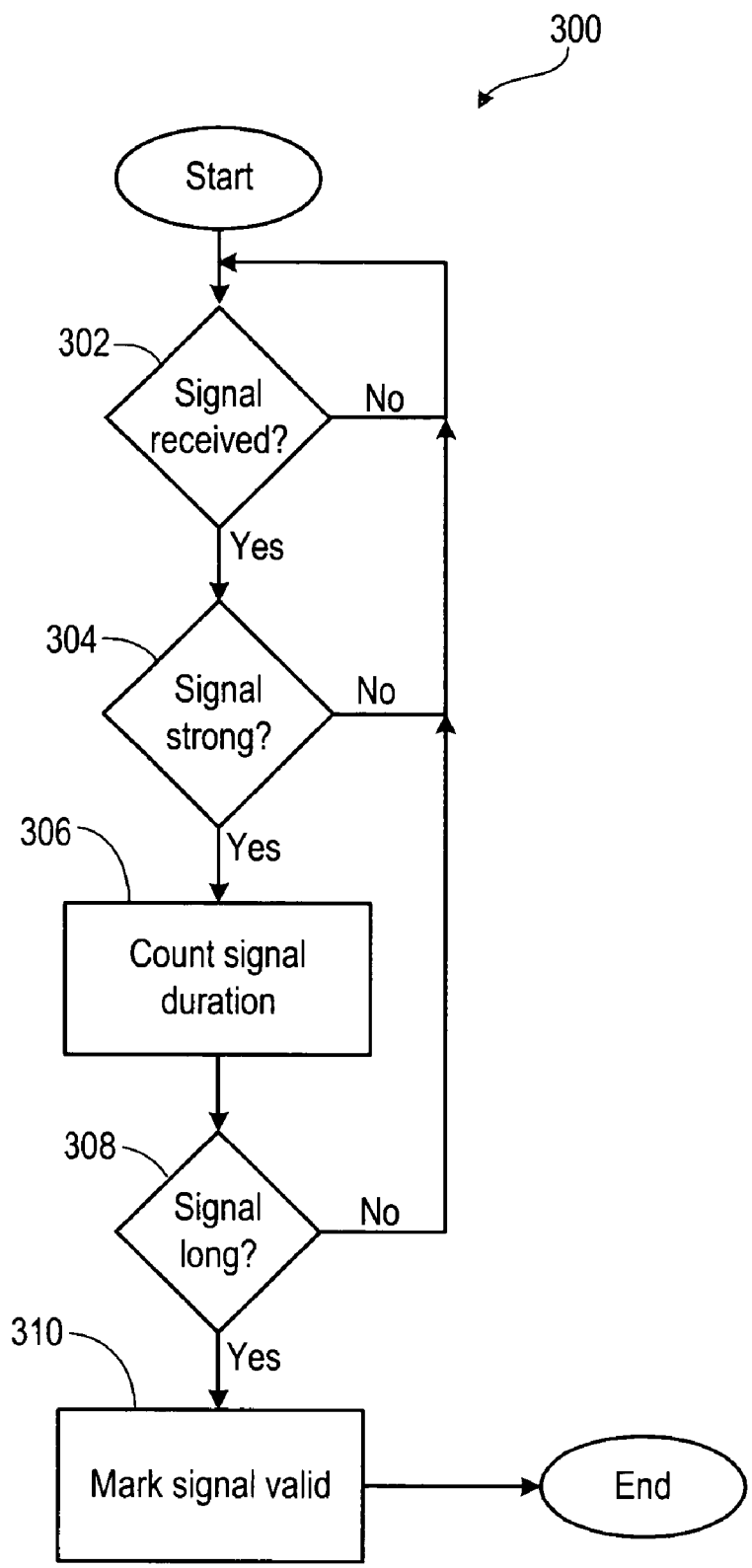
FIG. 3 is a flow chart of a process for identifying received neural signals.

FIG. 3 illustrates a process 300 for determining if a received signal is a valid indication of neural activity. The signal is recognized as a valid signal if it has a voltage greater than a predetermined level and if its duration is longer than a predetermined period. The process 300 checks if a signal is received, step 302. If no signal has been received, the computing device 120 continues monitor the receiver 122.

After a signal is received, the computer device 120 checks whether the signal has a voltage greater than the predetermined level, step 304. If the signal is not sufficiently strong, it is ignored and the computing device 120 continues to monitor the receiver 122. If the signal is sufficiently strong, the computing device 120 counts the duration of the signal, step 306. After counting the duration, the duration is compared with a predetermined duration, step 308. If the duration is longer than the predetermined duration, the signal is marked as a good signal, step 310. The computer 120 may then take a predetermined action. If the duration is shorter than the predefined duration, the signal is ignored. By comparing the recovered signal with the predefined threshold voltage level and the predefined duration, spurious signals can be eliminated.

Figure 4:
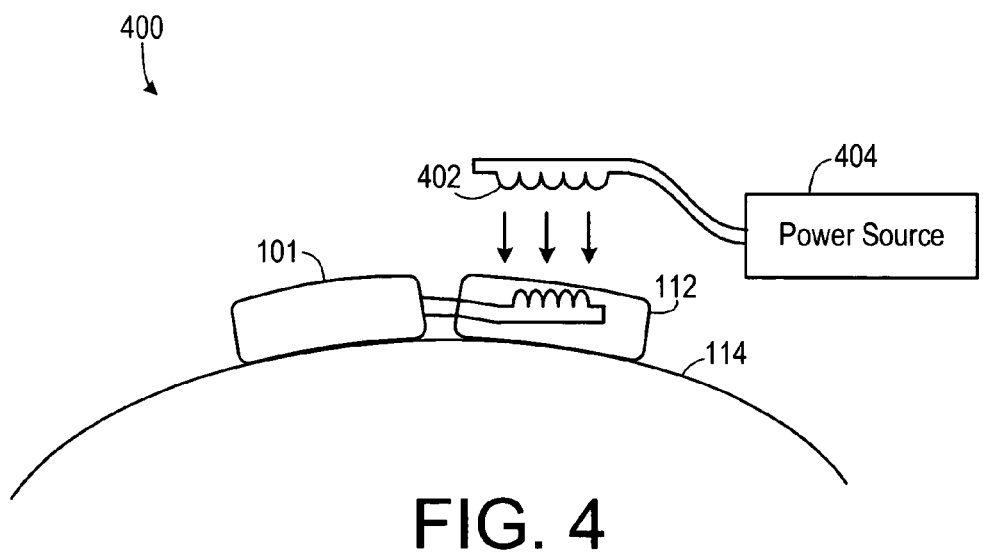
FIG. 4 illustrates working of a power induction circuit.

The inductive power supply 400 is shown in FIG. 4. The power induction circuit 112 is energized by electromagnetic radiation produced by an inductor 402 connected to a power source 404. The power source 404 may be powered by an external power supply, a battery, or other suitable sources. The power induction circuit 112 is exposed to the electromagnetic radiation and produces an electrical current to power the transponder 101. In an alternative embodiment, the transponder 101 may be directly connected to a power supply.

Figure 5:
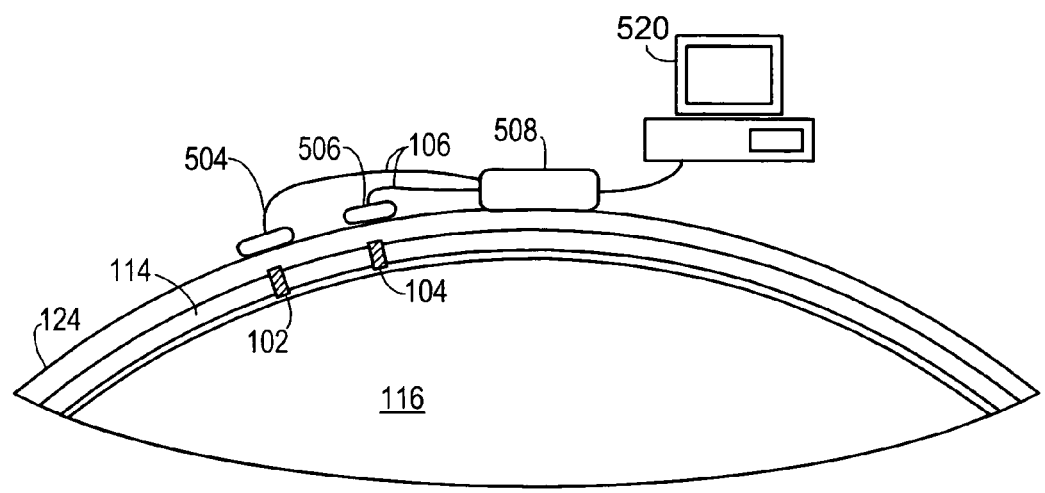
FIG. 5 is a cutaway view of an alternative embodiment of the invention.

In another embodiment, as shown in FIG. 5, the conductive skull screws 102 and 104 are implanted in the cranium 114 and under the scalp 124. Two surface electrodes 504 and 506 are placed on the top of the conductive skull screws 102 and 104 above the scalp 124. The surface electrodes 504 and 506 are connected to an amplifier 508, which may be connected directly to a computational device 520 or may be connected to a transmitter, as described above. The surface electrodes are secured to the scalp 124 using adhesives or other methods known to those skilled in the art. In this embodiment, the placement of the screws in the patient's skull provides a mechanism to improve transfer of neural signals through the skull, thereby improving signal reception during such diagnostic procedures, such electroencephalography (EEG).

Before the implantation of the conductive skull screws 102 and 104 a pre-operative assessment of the patient is conducted. The pre-operative assessment consists of assessing cognition using questions requiring a "yes" or "no" answer and acquiring knowledge of pre-morbid cognitive baseline, including the education level. After the assessment, a functional MRI (fMRI) is performed to determine if, where and when, neural activity exists. During the fMRI process, a patient is encouraged to visualize a performance of a specific movement. During the fMRI, a clinician records the region of the cortex where a neural signal occurs and this region is then associated with that specific movement.

The fMRI results guide implantation site selection. Two sites are selected: one for the active conductive skull screw and one for the neutral conductive skull screw. A craniotomy is performed over the target areas identified at surgery. Alignment with the active areas noted on the pre-operative fMRI.

After implantation, the invention is capable of detecting differential potentials in the order of few hundred microvolts between the conductive skull screws 102 and 104. The differential potential detected may have different frequencies, such as 5 Hz, 10 Hz, 20 Hz, 40 Hz, etc.

In view of the method being executable on a computing device, the present invention includes programs resident in a computer readable medium, where the programs direct a server or other computer device having a computer platform to perform the steps of the method. The computer readable medium can be the memory of the server, or can be in a connective database. Further, the computer readable medium can be in a secondary storage media that is loadable onto a wireless communications device computer platform, such as a magnetic disk or tape, optical disk, hard disk, flash memory, or other storage media as is known in the art.

While the invention has been particularly shown and described with reference to a embodiment shown herein, it will be understood by those skilled in the art that various changes in form and detail maybe made without departing from the spirit and scope of the present invention as set for the in the following claims. Furthermore, although elements of the invention may be described or claimed in the singular, the plural is contemplated unless limitation to the singular is explicitly stated.

What is claimed is:

1. An apparatus for interfacing neural signals emanating from inside a brain within a cranium, having a thickness, that is covered by a scalp with an external device, comprising:
   a. a first conductive skull screw, capable of being implanted in the cranium and under the scalp, having a constant outside diameter and having a predefined length that corresponds to the thickness of the cranium, but less than a length that would cause the first conductive skull screw to invade the brain when implanted into the cranium, the first conductive skull screw not including a head having a diameter wider than the constant outside diameter;
   b. a second conductive skull screw, capable of being implanted in the cranium and under the scalp, having a constant outside diameter and having a predefined length that corresponds to the thickness of the cranium, but less than a length that would cause the second conductive skull screw to invade the brain when implanted into the cranium, the second conductive skull screw not including a head having a diameter wider than the constant outside diameter;
   c. a transponder electrically coupled to the first conductive skull screw and to the second conductive skull screw, the transponder capable of being implanted between the cranium and the scalp, the transponder capable of detecting a differential electrical potential between the first conductive skull screw and the second conductive skull screw and generate a signal representative thereof, the transponder also capable of transmitting the signal;
   d. an external receiver that receives the signal from the transponder and generates an output corresponding to the signal; and e. a computer, in communication with the external receiver, that initiates a predetermined action that controls an external environment upon receiving the output from the external receiver and determining that the signal has a predetermined signal strength and duration so as to indicate attempted cortical control by a patient.

2. The apparatus of claim 1, wherein the transponder comprises:
   a. an amplifier that amplifies the signal;
   b. a transmitter that transmits the signal; and
   c. a power induction circuit that is capable of converting an electromagnetic signal into a current used to drive the amplifier and the transmitter.

3. The apparatus of claim 1, wherein the first conductive skull screw and the second conductive skull screw comprise stainless steel.

4. The apparatus of claim 1, wherein the predetermined action comprises moving a cursor on a computer monitor.

5. A method for communicating a neural signal inside a brain to a remote receiver, comprising the steps of:
   a. inserting a first conductive skull screw in a cranium under a scalp in a first location the first conductive skull screw having a substantially constant outside diameter and having a predefined length that corresponds to the thickness of the cranium, but less than a length that would cause the first conductive skull screw to invade the brain when implanted into the cranium, so that the first conductive skull screw does not extend beyond the scalp;
   b. inserting a second conductive skull screw in a cranium under the scalp in a second location, the second conductive skull screw having a substantially constant outside diameter and having a predefined length that corresponds to the thickness of the cranium, but less than a length that would cause the first conductive skull screw to invade the brain when implanted into the cranium, the first location and the second location chosen so that a change in neural electrical potential between the first conductive skull screw and the second conductive skull screw occurs when a patient performs a neural task, so that the second conductive skull screw does not extend beyond the scalp;
   c. implanting a transponder under the scalp, the transponder being electrically coupled to the first conductive skull screw and to the second conductive skull screw;
   d. detecting the change in neural electrical potential between the first conductive skull screw and the second conductive skull screw;
   e. transmitting a signal representative of the change in neural electrical potential from the transponder to the remote receiver;
   f. receiving the signal with an external receiver and generating an output from the external receiver when the signal is received;
   g. determining that the signal has a predetermined signal strength and duration so as to indicate attempted cortical control by a patient; and
   h. causing a predetermined action that controls an external environment to occur when the signal has a predetermined signal strength and duration.

6. The method of claim 5, further comprising the step of amplifying the differential potential before the transmitting step.

7. The method of claim 5, further comprising the steps of powering a transponder used to transmit the signal with a power induction circuit.

8. The apparatus of claim 5, wherein the predetermined action comprises moving a cursor on a computer monitor.

* * * * *